(12) United States Patent
Miyoshi et al.

(10) Patent No.: US 8,309,305 B2
(45) Date of Patent: Nov. 13, 2012

(54) METHOD FOR DISCRIMINATING BETWEEN NUCLEOTIDE SEQUENCES OF NUCLEIC ACIDS

(75) Inventors: Hayato Miyoshi, Kanagawa (JP); Yoshihide Iwaki, Kanagawa (JP); Toshihiro Mori, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 539 days.

(21) Appl. No.: 12/471,817

(22) Filed: May 26, 2009

(65) Prior Publication Data
US 2010/0047794 A1 Feb. 25, 2010

(30) Foreign Application Priority Data

May 27, 2008 (JP) ................................. 2008-137921

(51) Int. Cl.
*C12Q 1/68* (2006.01)
(52) U.S. Cl. ....................................................... 435/6.1
(58) Field of Classification Search .................. None
See application file for complete search history.

(56) References Cited

U.S. PATENT DOCUMENTS

| | | | |
|---|---|---|---|
| 5,348,853 A | 9/1994 | Wang et al. | |
| 5,766,890 A * | 6/1998 | Kacian et al. | 435/91.2 |
| 5,814,492 A | 9/1998 | Carrino et al. | |
| 6,238,868 B1 * | 5/2001 | Carrino et al. | 435/6.11 |
| 6,413,758 B1 * | 7/2002 | Xu et al. | 435/199 |
| 2003/0165913 A1 | 9/2003 | Wang et al. | |
| 2008/0118917 A1 | 5/2008 | Hardy et al. | |

FOREIGN PATENT DOCUMENTS

JP 2002-233379 A 8/2002

OTHER PUBLICATIONS

Fortina et al. (Mol Cell Probes. Aug. 1992;6(4):353-6).*
Spargo et al. (Mol Cell Probes. Aug. 1996;10(4):247-56).*
NEB (http://www.neb.com/nebecomm/tech_reference/polymerases/properties_dna_polymerases.asp, accessed Feb. 26, 2012).*
Notomi et al., "Loop-mediated isothermal amplification of DNA", Nucleic Acids Research, Oxford University Press, vol. 28, No. 12, pp. i-vii (1-7), Jun. 15, 2000, Surrey, Great Britain, XP002292090.
Chinese Office Action dated Jun. 29, 2012, for Chinese Application No. 200910202852.8, with English translation.
Parsons et al., "Detection of a mouse H-ras codon 61 mutation using a modified allele-specific competitive blocker PCR genotypic selection method", Mutagenesis, vol. 13, No. 6, 1998, pp. 581-588.
Sambrook et al., "Molecular Cloning: A Laboratory Manual", Science Press 2002, (Third Edition), p. 605, with English translation.

* cited by examiner

*Primary Examiner* — Christopher M. Babic
(74) *Attorney, Agent, or Firm* — Birch, Stewart, Kolasch & Birch, LLP (57) ABSTRACT

The present invention describes methods for discriminating between nucleotide sequences of first and second nucleic acids, including: providing a reaction solution, including a deoxynucleotide triphosphate, a DNA polymerase with strand displacement ability, a template nucleic acid fragment, a primer, and a mask oligo; incubating the reaction solution, obtaining a polymerase reaction, and producing an amplification product; detecting the amplification product to discriminate between the nucleotide sequences, wherein the primer is complementary to the first nucleic acid, the mask oligo hybridizes to the nucleotide sequence portion of the first and second nucleic acid, wherein the mask oligo is more complementary to the second nucleic acid than to the first nucleic acid, and wherein the mask oligo is not an origin of an elongation reaction with the polymerase, and a primer portion and a mask oligo portion hybridize to the same regions on the first and second nucleic acid.

19 Claims, 4 Drawing Sheets

SEQUENCE LISTING

<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: Synthetic DNA

<400> SEQUENCE: 1
atcgtggcca tcgcct                    16

<210> SEQ ID NO 2
<211> LENGTH: 17

-continued

```
<212> TYPE: DNA
<213> ORGANISM: Artificial Sequence
<220> FEATURE:
<223> OTHER INFORMATION: Synthetic DNA

<400> SEQUENCE: 2
ccagcgaagt cacgaac                                                    17

<210> SEQ ID NO 3
<211> LENGTH: 17
<212> TYPE: DNA
<213> ORGANISM: Artificial Sequence
<220> FEATURE:
<223> OTHER INFORMATION: Synthetic DNA

<400> SEQUENCE: 3
cgtggccatc gcccgga                                                    17

<210> SEQ ID NO 4
<211> LENGTH: 17
<212> TYPE: RNA
<213> ORGANISM: Artificial Sequence
<220> FEATURE:
<223> OTHER INFORMATION: Synthetic RNA

<400> SEQUENCE: 4
cguggccauc gcccgga                                                    17

<210> SEQ ID NO 5
<211> LENGTH: 120
<212> TYPE: DNA
<213> ORGANISM: Artificial Sequence
<220> FEATURE:
<223> OTHER INFORMATION: Synthetic DNA

<400> SEQUENCE: 5
ggtgctggcc accgtgggag gcaacctgct ggtcatcgtg gccatcgcct ggactccgag     60
actccagacc atgaccaacg tgttcgtgac ttcgctggcc gcagccgacc tggtgatggg    120

<210> SEQ ID NO 6
<211> LENGTH: 120
<212> TYPE: DNA
<213> ORGANISM: Artificial Sequence
<220> FEATURE:
<223> OTHER INFORMATION: Synthetic DNA

<400> SEQUENCE: 6
cccatcacca ggtcggctgc ggccagcgaa gtcacgaaca cgttggtcat ggtctggagt     60
ctcggagtcc aggcgatggc cacgatgacc agcaggttgc ctcccacggt ggccagcacc    120
```

METHOD FOR DISCRIMINATING BETWEEN NUCLEOTIDE SEQUENCES OF NUCLEIC ACIDS

TECHNICAL FIELD

The present invention relates to a method for discriminating between the nucleotide sequences of nucleic acids. More specifically, the present invention relates to a method for carrying out detection of a specific sequence contained in the DNA of a sample, detection of genetic polymorphisms, the analysis of single nucleotide polymorphisms (SNPs) and the like, by utilizing a nucleic acid amplification method.

BACKGROUND ART

As a result of genomic analyses, an attempt has been actively made to apply genomic information regarding genetic polymorphisms and the like to the medical field.

For example, it is said that single nucleotide polymorphisms (SNPs) exist in 1 out of 1,000 nucleotides. The SNPs are considered to cause individual differences and differences in individual characteristics or congenital predispositions. Moreover, it is being revealed that factor genes are associated, as risk factors, with diseases (diabetes, hypertension, etc.) on which environmental factors had previously been considered to act at a relatively high rate. Also, it has being revealed that many such factor genes relate to single nucleotide polymorphisms. Hence, SNPs analysis has been considered to result in medication and treatment that are adapted to the physical constitutions of individuals (Taylor-made medical treatment), and thus the SNPs analysis has got a lot of attention.

The subtypes of bacteria or viruses, such as HCV, influenza virus or *Helicobacter pylori*, have been considered to be certain types of polymorphisms. The therapeutic effects of various types of agents are different depending on such subtypes. Accordingly, the analyses of the polymorphisms of such viruses and the like would give information important for selection of treatment methods.

As a method for discriminating between the nucleotide sequences of nucleic acids, there has been known a method for carrying out a nucleic acid amplification reaction using DNA polymerase and primers designed to have sequences complementary to sequences to be detected.

As a method of amplifying a nucleic acid, a polymerase chain reaction (PCR) has been widely known. In order to amplify a target nucleic acid sequence of interest, the PCR method comprises the following three steps: a step of denaturing double-stranded DNA used as a template to convert it to single-stranded DNA (denaturation step); a step of annealing a primer to the single-stranded DNA (annealing step); and elongating a complementary stand using the primer as an origin (elongation step). In an ordinary PCR method, a thermal cycler is used, and the denaturation step, the annealing step and the elongation step are carried out at different temperatures. However, in order to carry out a nucleic acid amplification reaction at the 3 different types of temperatures, it is necessary to precisely control temperatures, and thereby it becomes difficult to carry out tests simply using small devices. Moreover, the PCR method has also been problematic in that time loss increases as the number of the cycle increases.

Under the aforementioned circumstances, a nucleic acid amplification method that can be carried out under isothermal conditions has been developed. Examples of such a nucleic acid amplification method include RCA (Rolling Circle Amplification: Proc. Natl. Acad. Sci, Vol. 92, 4641-4645 (1995)), an SDA method (Strand Displacement Amplification; JP Patent Publication (Kokai) No. 5-130870 A (1993)), ICAN (Isothermal and Chimeric primer-initiated Amplification of Nucleic acids), LAMP (Loop-Mediated Isothermal Amplification of DNA; Bio Industry, Vol. 18, No. 2 (2001)), NASBA (Nucleic acid Sequence-based Amplification method; Nature, 350, 91-(1991)), and TMA (Transcription mediated amplification method; J. Clin Microbiol. Vol. 31, 3270-(1993)).

However, these methods have been problematic in that they cause high costs for the combined use of exonuclease, RNaseH, reverse transcriptase or the like with polymerase, or for the use of specific primers, and also in that it is extremely difficult to design primers.

JP Patent Publication (Kokai) No. 2002-233379 describes a method for amplifying the DNA of a region of interest by performing a reaction at an isothermal temperature using at least a pair of oligonucleotide primers in the presence of DNA polymerase having strand displacement ability. However, the method described in JP Patent Publication (Kokai) No. 2002-233379 has been problematic in that it requires a relatively long reaction time.

Furthermore, methods for discriminating between the nucleotide sequences of nucleic acids using a nucleic acid amplification reaction share a problem that such amplification reaction often takes place even when primers are not completely complementary to a target sequence (non-specific amplification). For example, in the case of discriminating between single nucleotide polymorphisms, a difference between a nucleic acid as a target to be discriminated and a nucleic acid as a non-target to be discriminated is only one nucleotide. As a result, the aforementioned non-specific amplification significantly takes place. Whether or not such non-specific amplification takes place depends also on subtle conditions such as apparatuses or surrounding environments. Accordingly, it is difficult to suppress such non-specific amplification.

DISCLOSURE OF THE INVENTION

It is an object of the present invention to provide a method for discriminating between nucleic acid sequences with high accuracy by utilizing a method for specifically amplifying nucleic acid sequences under isothermal conditions. It is another object of the present invention to realize the aforementioned method by designing primers more simply than before.

The present inventors have used at least one type of oligonucleotide (hereinafter referred to as a "primer") substantially complementary to a first nucleic acid, and at least one type of oligonucleic acid (hereinafter referred to as a "mask oligo") that is designed such that it hybridizes to the nucleotide sequence portions of the first nucleic acid and the second nucleic acid to be discriminated, such that it is more complementary to the second nucleic acid than to the first nucleic acid, and such that it does not become an origin of an elongation reaction with polymerase. Moreover, the inventors have designed the aforementioned primer and the aforementioned mask oligo such that a portion of the primer and a portion of the mask oligo can hybridize to the same regions on the first nucleic acid and the second nucleic acid. As a result, the inventors have found that the difference between the nucleotide sequences of the two types of nucleic acids can be simply and rapidly identified with high accuracy by utilizing an isothermal amplification method.

Furthermore, the present inventors have performed an amplification reaction in a reaction solution comprising deoxynucleotide triphosphate, DNA polymerase having strand displacement ability, a divalent cation, a surfactant, oligonucleotide primers, and a nucleic acid fragment used as a template. As a result, the inventors have found that a nucleic acid sequence can be specifically amplified under isothermal conditions by using the oligonucleotide primers that do not adopt a complicated structure as used in the conventional isothermal amplification methods (for example, these primers do not need to adopt a chimeric structure used in the ICAN method or a loop structure used in the LAMP method), thereby completing the present invention.

The present invention provides a method for discriminating between the nucleotide sequence of a first nucleic acid and the nucleotide sequence of a second nucleic acid by a nucleic acid amplification method that is performed under substantially isothermal conditions, wherein (1) at least one type of oligonucleotide (hereinafter "primer") substantially complementary to the first nucleic acid, and (2) at least one type of oligonucleic acid (hereinafter "mask oligo") that is designed such that it hybridizes to the nucleotide sequence portions of the first nucleic acid and the second nucleic acid to be discriminated, such that it is more complementary to the second nucleic acid than to the first nucleic acid, and such that it does not become an origin of an elongation reaction with polymerase, are used, the method being characterized in that a portion of the primer and a portion of the mask oligo hybridize to the same regions on the first nucleic acid and the second nucleic acid.

Preferably, the regions on the first nucleic acid and the second nucleic acid, to which both the primer and the mask oligo hybridize, hybridize to a region comprising the 3'-terminus of the primer.

Preferably, the regions on the first nucleic acid and the second nucleic acid, to which both the primer and the mask oligo hybridize, hybridize to a region comprising the 5'-terminus of the mask oligo.

Preferably, the primer is more complementary to the first nucleic acid than to the second nucleic acid.

Preferably, the primer is designed to hybridize to the first nucleic acid or the second nucleic acid via only a consecutive region at the 3'-terminus.

Preferably, there is a single nucleotide polymorphism relationship between the first nucleic acid and the second nucleic acid, and at least two types of primers are used that are designed such that they are complementary to each different strand of double-stranded DNA, and such that one oligonucleotide primer is complementary to a region existing on the 3'-terminal side of a sequence homologous with the other oligonucleotide primer on the DNA strand.

Preferably, a reaction solution comprising at least one type of deoxynucleotide triphosphate, at least one type of DNA polymerase having strand displacement ability, and a nucleic acid fragment used as a template is incubated to carry out a polymerase reaction using the 3'-terminus of the primer as an origin, so as to amplify the nucleic acid fragment, thereby discriminating between the nucleotide sequence of the first nucleic acid and the nucleotide sequence of the second nucleic acid.

Preferably, a difference in amplification rates is used to discriminate between the nucleotide sequence of the first nucleic acid and the nucleotide sequence of the second nucleic acid.

Preferably, the reaction solution further comprises at least 0.01% of a surfactant.

More preferably, the reaction solution further comprises at least 0.05% of a surfactant.

Preferably, the surfactant is a nonionic surfactant.

Preferably, the HLB value of the nonionic surfactant is 12 or greater.

Preferably, the HLB value of the nonionic surfactant is 14 or greater.

Preferably, the nonionic surfactant is selected from among polyoxyethylene sorbitan fatty acid ester nonionic surfactants and polyoxyethylene alkyl ether nonionic surfactants.

More preferably, the polyoxyethylene sorbitan fatty acid ester nonionic surfactant is a polyoxyethylene sorbitan monofatty acid ester.

More preferably, the nonionic surfactant is represented by the following chemical formula:

wherein $x+y+z+w=20$; and R represents an alkyl group containing 12 to 18 carbon atoms.

Preferably, the polyoxyethylene sorbitan fatty acid ester nonionic surfactant is at least one selected from among polyoxyethylene (20) sorbitan monolaurate, polyoxyethylene (20) sorbitan monopalmitate, polyoxyethylene (20) sorbitan monostearate, and polyoxyethylene (20) sorbitan monooleate.

Preferably, the reaction solution further comprises a divalent cation.

Preferably, the reaction solution further comprises a melting temperature adjuster.

Preferably, at least one type of polymerase having strand displacement ability is selected from the group consisting of 5'→3' exonuclease-deficient Bst DNA polymerase derived from *Bacillus stearothermophilus*, 5'→3' exonuclease-deficient Bca DNA polymerase derived from *Bacillus caldotenax*, and 5'→3' exonuclease-deficient Vent. DNA polymerase derived from *Thermococcus litoralis*.

Preferably, the reaction solution is incubated under substantially isothermal conditions.

Preferably, the reaction solution is incubated under substantially isothermal conditions from 50° C. to 1000.

Preferably, the time required for the incubation of the reaction solution under isothermal conditions is 60 minutes or shorter.

According to the present invention, the difference between the nucleotide sequences of two types of nucleic acids can be simply and rapidly identified with high accuracy by utilizing a nucleic acid amplification method. More specifically, the presence of a mask oligo suppresses non-specific amplification of a primer, and thus it becomes possible to determine the nucleotide sequence of a nucleic acid with high accuracy by utilizing an amplification reaction.

BEST MODE FOR CARRYING OUT THE INVENTION

The present invention will be described more in detail below.

The present invention relates to a method for discriminating between the nucleotide sequence of a first nucleic acid and the nucleotide sequence of a second nucleic acid by a nucleic acid amplification method that is performed under substantially isothermal conditions, which uses (1) at least one type of oligonucleotide (hereinafter referred to as a "primer") substantially complementary to the first nucleic acid, and (2) at least one type of oligonucleic acid (hereinafter referred to as a "mask oligo") that is designed such that it hybridizes to the nucleotide sequence portions of the first nucleic acid and the second nucleic acid to be discriminated, such that it is more complementary to the second nucleic acid than to the first nucleic acid, and such that it does not become an origin of an elongation reaction with polymerase; the aforementioned method being characterized in that a portion of the primer and a portion of the mask oligo hybridize to the same regions on the first nucleic acid and the second nucleic acid.

In a preferred embodiment of the present invention, there are used (1) at least one type of oligonucleotide (hereinafter referred to as a "primer") that is substantially complementary to a first nucleic acid but is not complementary to a second nucleic acid (hereinafter referred to as a "primer"), and (2) at least one type of oligonucleic acid (hereinafter referred to as a "mask oligo") that is designed such that it hybridizes to the nucleotide sequence portions of the first nucleic acid and the second nucleic acid to be discriminated, such that it is more complementary to the second nucleic acid than to the first nucleic acid, and such that it does not become an origin of an elongation reaction with polymerase, wherein the primer and the mask oligo are designed such that a portion of the primer and a portion of the mask oligo hybridize to the same regions on the first nucleic acid and the second nucleic acid, and a nucleic acid amplification reaction is carried out by incubating a reaction solution comprising at least one type of deoxynucleotide triphosphate, at least one type of DNA polymerase having strand displacement ability, and a nucleic acid fragment used as a template, so as to discriminate between the nucleotide sequence of the first nucleic acid and the nucleotide sequence of the second nucleic acid. Moreover, the difference between the nucleotide sequence of the first nucleic acid and the nucleotide sequence of the second nucleic acid can be identified by the difference in amplification rates.

Next the ingredients used in the present invention will be described below.

(1) Deoxynucleotide Triphosphate

Deoxynucleotide triphosphate is used as a substrate for an elongation reaction Specifically, a mixture of dATP, dCTP, dGTP and dTTP is preferably used. Deoxynucleotide triphosphate may comprise analogs of dNTP (for example, 7-deaza-dGTP, etc.).

In addition, the final concentration of such deoxynucleotide triphosphate (a mixture of dATP, dCTP, dGTP and dTTP) is within the range from 0.1 mM to 3.0 mM, preferably from 0.75 mM to 3.0 mM, more preferably from 1.0 mM to 2.0 mM, and particularly preferably from 1.0 mM to 1.5 mM.

(2) Polymerase Having Strand Displacement Ability

In the present invention, polymerase having strand displacement ability is used. The term "strand displacement ability" is used in the present specification to mean an activity of performing DNA replication using a nucleic acid sequence as a template while displacing a DNA strand, so as to release a complementary strand annealed to a template strand; namely an activity of performing strand displacement. Specific examples of such polymerase having strand displacement ability include 5'→3' exonuclease-deficient Bst DNA polymerase derived from *Bacillus stearothermophilus*, 5'→3' exonuclease-deficient Bca DNA polymerase derived from *Bacillus caldotenax*, and 5'→3' exonuclease-deficient Vent. DNA polymerase derived from *Thermococcus litoralis*, but examples are not limited thereto. Such polymerase having strand displacement ability may be either a naturally-occurring protein or a recombinant protein produced by genetic engineering.

(3) Divalent Cation

In the present invention, a divalent cation can be used depending on the metallic requirement level of enzyme used, and the like. As such a divalent cation, magnesium salts and other metal salts can be used. For example, magnesium chloride, magnesium acetate, magnesium sulfate and the like can be used. The final concentration of such a divalent cation is within the range preferably from 1 mM to 20 mM, and more preferably from 2 mM to 10 mM.

(4) Surfactant

In the present invention, a surfactant is added into a reaction solution. Using such a surfactant, the advantageous effect of the present invention that is prevention of non-specific amplification of nucleic acids can be achieved. The type of the surfactant used in the present invention is not particularly limited. Examples of the surfactant that can be used in the present invention include: anionic surfactants such as alkylbenzene sulfonate, lauryl sulfate ester (SDS), octyl sulfosuccinate or stearic acid soap; nonionic surfactants such as sorbitan fatty acid ester, POE sorbitan fatty acid ester (Tween, etc.), POE alkyl ether (Brij, etc.), POE alkyl phenyl ether (Triton, etc.), nonylphenol, lauryl alcohol, polyethylene glycol, a polyoxyethylene-polyoxypropylene block polymer, POE alkylamine or POE fatty acid bisphenyl ether; cationic surfactants such as cetylpyridinium chloride, lauryl dimethyl benzyl ammonium chloride or stearyl trimethyl ammonium chloride; and ampholytic surfactants such as alkyl dimethyl amine oxide or alkyl carboxy betaine. The amount of the surfactant used is not particularly limited, as long as the effect of the present invention can be achieved. The amount of the surfactant used is preferably 0.01% or more, more preferably 0.05% or more, and further preferably 0.1% or more. The upper limit of the amount of the surfactant used is not particularly limited. It is generally 10% or less, preferably 5% or less, and more preferably 1% or less.

Among such surfactants, the use of nonionic surfactants is particularly preferable. Among the nonionic surfactants, a nonionic surfactant with strong hydrophilicity is preferable, and in terms of HLB value, a nonionic surfactant having an HLB value of 12 or greater is preferable. Such an HLB value is more preferably 14 or greater. The upper limit of the HLB value that is preferably applied is 20. The upper limit of the HLB value is more preferably 17 or less, and further preferably from 14 to 17. Taking into account the structure of a surfactant, the surfactant used in the present invention is preferably selected from among polyoxyethylene sorbitan fatty acid esters and polyoxyethylene alkyl ethers. Among such polyoxyethylene sorbitan fatty acid esters, those having only one fatty acid ester are preferable. An example of such compound is represented by the following structural formula:

wherein x+y+z+w 20; and R represents an alkyl group containing 12 to 18 carbon atoms.

The position of an alkyl group is not particularly limited. The following structures may also be preferably used.

wherein x+y+z+w=20, R is an alkyl group having a carbon number of 12 to 18.

The surfactants represented by the above-descried formulae include nonionic surfactants called polyoxyethylene sorbitan fatty acid esters. Examples of such polyoxyethylene sorbitan fatty acid ester nonionic surfactants include polyoxyethylene (20) sorbitan monolaurate, polyoxyethylene (20) sorbitan monopalmitate, polyoxyethylene (20) sorbitan monostearate, and polyoxyethylene (20) sorbitan monooleate. (Product names: Tween20, Tween40, Tween60, Tween80, etc.). The amount of such a nonionic surfactant used is not particularly limited. It is preferably 0.01% or more, more preferably 0.05% or more, and further preferably 0.1% or more. In the present invention, a surfactant may be added into a reaction solution. Using a surfactant, the effect of preventing non-specific amplification of nucleic acids may be achieved. The type of a surfactant that can be used in the present invention is not particularly limited. Examples of the surfactant that can be used in the present invention include: sodium alkylbenzene sulfonate, sodium dodecyl sulfate (SDS), octyl sulfosuccinate or stearic acid soap; nonionic surfactants such as sucrose fatty acid ester sorbitan fatty acid esters, POE sorbitan fatty acid esters (Tween20, Tween40, Tween60, Tween80, etc.), fatty acid alkanolamide, POE allyl ethers (Brij35, Brij58, etc.), POE alkyl phenyl ethers (Triton X-100, Triton X-114, Nonidet P40, etc.), nonylphenol, lauryl alcohol, polyethylene glycol, a polyoxyethylene-polyoxypropylene block polymer, POE alkylamine or POE fatty acid bisphenyl ether; and cationic surfactants such as cetyl pyridinium chloride, lauryl dimethyl benzyl ammonium chloride or stearyl trimethyl ammonium chloride. The amount of the surfactant used is not particularly limited, as long as the effect of the present invention can be achieved. The amount of the surfactant used is preferably 0.01% or more, more preferably 0.05% or more, and further preferably 0.1% or more. The upper limit of the amount of the surfactant used is not particularly limited. It is generally 10% or less, preferably 5% or less, and more preferably 1% or less.

Among such surfactants, the use of nonionic surfactants is particularly preferable. Among others, it is particularly preferable to use any one of the POE sorbitan fatty acid ester, POE alkylphenol ether, and POE alkyl ether. As stated above, the type of a nonionic surfactant is not particularly limited. The amount of a nonionic surfactant used is not particularly limited, either. It is preferably 0.01% or more, more preferably 0.05% or more, and further preferably 0.1% or more.

(5) Oligonucleotides (a) Oligonucleotide Primer

The oligonucleotide primer used in the present invention is defined as an oligonucleotide having the property of extending a DNA stand from the 3'-terminus thereof by the action of DNA polymerase, when it is annealed to DNA acting as a template. As an oligonucleotide primer used in the present invention, a primer consisting of a deoxyribonucleotide or a ribonucleotide may be used. Moreover, a primer comprising a modified ribonucleotide or a modified deoxyribonucleotide may also be used.

In the present invention, at least one type of oligonucleotide primer complementary to a first nucleic acid is used. More preferably, at least one type of oligonucleotide primer that is complementary to a first nucleic acid but is not complementary to a second nucleic acid is used. Further preferably, two types of oligonucleotide primers (a set of oligonucleotide primers) comprising at least one type of oligonucleotide primer that is complementary to a first nucleic acid but is not complementary to a second nucleic acid are used. The term "a set of oligonucleotide primers" is used herein to mean a combination of at least two types of oligonucleotide primers that are designed such that the two types of primers are complementary to each different strand of double-stranded DNA, and such that one oligonucleotide primer is complementary to a region existing on the 3'-terminal side of a sequence homologous with the other oligonucleotide primer on the DNA strand (that are designed such that a sequence homologous with one oligonucleotide primer exists in a region on the 5'-terminal side of a sequence complementary to the other oligonucleotide primer).

Furthermore, the aforementioned oligonucleotide primers do not require a complicated structure as used in the conventional isothermal amplification reactions. The present invention is characterized in that it enables performing an isothermal amplification reaction using at least one set of primers used in ordinary PCR reactions. Specifically, these primers do not have a structure for forming a loop structure used in the LAMP method or the like, in which the 5'-terminus becomes complementary to a portion extended from the 3'-terminus.

That is to say, a consecutive region at the 3'-terminus of the primer is complementary to a template nucleic acid. Further, these primers do not have a complicated structure used in the SDA method or the ICAN method, in which the primer is cleaved during the reaction and the cleaved 3'-terminus becomes a new synthetic origin.

The length of an oligonucleotide primer is not particularly limited. The length consists of generally approximately 10 to 100 nucleotides, preferably approximately 10 to 50 nucleotides, and more preferably approximately 10 to 40 nucleotides.

Such an oligonucleotide primer can be synthesized by a phosphoamidite method using a commercially available DNA synthesizer (for example, Model 394 DNA synthesizer manufactured by Applied Biosystems, etc.).

The amount of such an oligonucleotide primer used in a reaction solution is preferably 0.1 µM or more, more preferably 1 µM or more, and particularly preferably 1.5 µM or more.

(b) Mask Oligo

The present invention further uses at least one oligo nucleic acid (hereinafter also referred to as a "mask oligo") that is designed such that it hybridizes to the nucleotide sequence portions of the first nucleic acid and the second nucleic acid to be discriminated, such that it is more complementary to the second nucleic acid than to the first nucleic acid, and such that it does not become an origin of nucleic acid amplification.

Examples of a means for preventing the oligo nucleic acid from becoming an origin of nucleic acid amplification include a method of modifying the 3'-terminus of the oligo nucleic acid (for example, by phosphorylation, amination, biotinylation, labeling with various types of fluorochromes, etc.), and a method using RNA, PNA (peptide nucleic acid) or LNA (locked nucleic acid) as an oligo nucleic acid.

Further, the mask oligo used in the present invention is designed such that a part of or the entire region hybridizing to the first nucleic acid or the second nucleic acid becomes identical to a part of or the entire region to which the primer hybridizes.

Preferably, the mask oligo used in the present invention is designed to hybridize to a region on the first nucleic acid or the second nucleic acid, to which at least a nucleotide at the 3'-terminus of the primer hybridizes.

More preferably, the mask oligo used in the present invention is designed to hybridize to a region on the first nucleic acid or the second nucleic acid, to which at least two nucleotides on the 3'-terminal side of the primer hybridize.

Further preferably, the mask oligo used in the present invention is designed to hybridize to a region on the first nucleic acid or the second nucleic acid, to which at least five nucleotides on the 3'-terminal side of the primer hybridize.

Still further preferably, the mask oligo used in the present invention is designed to hybridize to a region on the first nucleic acid or the second nucleic acid, to which at least eight nucleotides on the 3'-terminal side of the primer hybridize.

The region on the mask oligo hybridizing to a region on the first nucleic acid or the second nucleic acid, to which the primer hybridizes, is not particularly limited. In general, it is a region on the 5'-terminal side of the mask oligo.

Preferably, at least a nucleotide at the 5'-terminus of the mask oligo hybridizes to a region on the first nucleic acid or the second nucleic acid, to which at least a nucleotide at the 3'-terminus of the primer hybridizes.

More preferably, at least two nucleotides on the 5'-terminal side of the mask oligo hybridize to a region on the first nucleic acid or the second nucleic acid, to which at least two nucleotides on the 3'-terminal side of the primer hybridize.

Further preferably, at least five nucleotides on the 5'-terminal side of the mask oligo hybridize to a region on the first nucleic acid or the second nucleic acid, to which at least five nucleotides on the 3'-terminal side of the primer hybridize.

Still further preferably, at least eight nucleotides on the 5'-terminal side of the mask oligo hybridize to a region on the first nucleic acid or the second nucleic acid, to which at least eight nucleotides on the 3'-terminal side of the primer hybridize.

The Tm of the mask oligo used in the present invention is not particularly limited. In general, the Tm is designed to be within ±20° C. of the Tm of the primer. More preferably, the Tm of the mask oligo is designed, such that it becomes higher than a temperature that is 10° C. lower than the Tm of the primer and such that it becomes lower than a temperature that is 20° C. higher than the Tm of the primer. It is to be noted that such Tm can be calculated by a nearest neighbor method. For example, the Na+ concentration may be set at 50 mM.

The length of the mask oligo used in the present invention is not particularly limited. It is a length consisting of generally approximately 5 to 100 nucleotides, preferably approximately 10 to 50 nucleotides, and more preferably approximately 10 to 40 nucleotides.

The mask oligo used in the present invention can be synthesized by a phosphoamidite method using a commercially available DNA synthesizer (for example, Model 394 DNA synthesizer manufactured by Applied Biosystems, etc.).

The amount of the mask oligo used in the present invention is preferably 0.1 µM or more, more preferably 1 µM or more, and particularly preferably 1.5 µM or more, in a reaction solution.

A portion of the primer and a portion of the mask oligo hybridize to the same regions on the first nucleic acid and the second nucleic acid to be discriminated. This same region may consist of 1 nucleotide, more preferably 3 or more nucleotides, and particularly preferably 6 or more nucleotides.

With regard to the amount ratio of the mask oligo to the primer, the mask oligo is used at a percentage of preferably 10% or more, more preferably 50% or more, and particularly preferably 100% or more, with respect to the amount of the primer.

(6) Nucleic Acid Fragment Used as Template

The nucleic acid (DNA or RNA) used as a template in the present invention may be any one of genomic DNA, cDNA, synthetic DNA, mRNA, and total RNA. A nucleic acid prepared from a sample that possibly contains a nucleic acid used as a template may be used, or a sample possibly containing a nucleic acid used as a template may be directly used. The type of a sample containing a nucleic acid used as a template is not particularly limited. Examples of such a sample include body fluids (for example, whole blood, serum, urine, cerebrospinal fluid, seminal fluid, saliva, etc.), tissues (for example, cancer tissues, etc.), organism-derived samples such as a cell culture, nucleic acid-containing samples such as virus, bacteria, mold, yeast, plants and animals, samples in which microorganisms are possibly mixed (for example, food products, etc.), and environmental samples such as soil and drainage. When a nucleic acid is prepared from the aforementioned samples, the preparation method is not particularly limited. For example, methods known to persons skilled in the art, such as a treatment with a surfactant, an ultrasonic treatment, or purification using glass beads, may be applied. Purification of a nucleic acid from such a sample can be carried out by phenol extraction, chromatography, gel electrophoresis, density gradient centrifugation, etc.

When a nucleic acid having a sequence derived from RNA is to be amplified, the method of the present invention can be carried out using, as a template, cDNA synthesized by a reverse transcription reaction using the RNA as a template. A primer used in such a reverse transcription reaction may be a primer having a nucleotide sequence complementary to specific template RNA, or an oligo dT primer, or a primer having a random sequence. The length of such a primer used in reverse transcription is preferably approximately 6 to 100 nucleotides, and more preferably approximately 9 to 50 nucleotides. The type of an enzyme used in the reverse transcription reaction is not particularly limited, as long as it has an activity of synthesizing cDNA using RNA as a template. For example, reverse transcriptase from avian myeloblastosis virus (AMV RTase), reverse transcriptase from Moloney murine leukemia virus (MMLV RTase), Rous-associated virus 2 reverse transcriptase (RAV-2 RTase) can be used. In addition, strand displacement-type DNA polymerase having a reverse transcription activity can also be used.

In the present invention, double-stranded DNA such as genomic DNA or a nucleic acid amplification fragment, and single-stranded DNA such as cDNA prepared form RNA via a reverse transcription reaction can be used as template DNA. The aforementioned double-stranded DNA may be denatured to single-stranded DNA, and it may be then used in the method of the present invention. Otherwise, such double-stranded DNA may also be used in the method of the present invention without performing such denaturation.

(7) Melting Temperature Adjuster

A melting temperature adjuster can be added to the reaction solution in the present invention. Specific examples of such a melting temperature adjuster include dimethyl sulfoxide (DMSO), betaine, formamide, glycerol, tetraalkylammonium salts, and a mixture of two or more types of these compounds. The amount of such a melting temperature adjuster used is not particularly limited. When the melting temperature adjuster is DMSO, formamide, or glycerol, it may be generally contained at a percentage of 10% or less in a reaction solution.

Betaine or tetraalkylammonium salts may be added in a concentration of approximately 0.2 to 3.0 M, and preferably approximately 0.5 to 1.5 M to a reaction solution.

(8) Buffer Component

The reaction solution used in the present invention may comprise a buffer component The type of such a buffer component is not particularly limited. For example, bicine, tricine, Hepes, Tris, phosphate (sodium phosphate, potassium phosphate, etc.), and the like may be used. The final concentration of a buffer component is within the range from 5 mM to 100 mM, and particularly preferably from 10 mM to 50 mM. The pH value of the buffer component depends on the optimal pH of an enzyme used in an amplification reaction. It is generally from pH 6.0 to 9.0, and particularly preferably from pH 7.0 to 9.0.

(9) Method of the Present Invention for Discriminating Between Nucleotide Sequences of Nucleic Acids Next the method of the present invention for discriminating between the nucleotide sequences of nucleic acids will be described. In the present invention, a reaction solution is incubated, which comprises: (1) at least two types of primers comprising at least one type of primer that is complementary to a fist nucleic acid but is not complementary to a second nucleic acid; (2) at least one oligonucleic acid that is designed such that it hybridizes to the nucleotide sequence portions of the first nucleic acid and the second nucleic acid to be discriminated, such that it is more complementary to the second nucleic acid than to the first nucleic acid, and such that it does not become an origin of nucleic acid amplification; (3) at least one type of deoxynucleotide triphosphate; (4) at least one type of DNA polymerase having strand displacement ability; and (5) a nucleic acid fragment used as a template. Thereby, a polymerase reaction is carried out using the 3'-terminus of the aforementioned primer as an origin, so as to amplify the nucleic acid fragment. Herein, nucleic acid amplification takes place rapidly for the first nucleic acid, whereas such nucleic acid amplification does not take place or takes place slowly. By this phenomenon, the difference between the nucleotide sequence of the first nucleic acid and the nucleotide sequence of the second nucleic acid can be identified. In the present invention, a step of amplifying a nucleic acid can be preferably carried out under substantially isothermal conditions. The temperature for incubation of the reaction solution is preferably 50° C. or more, and more preferably 55° C. or more. The reaction solution can be incubated around 60° C., for example. The temperature range is preferably from approximately 50° C. to approximately 70° C., and more preferably from approximately 55° C. to approximately 65° C. In this case, the non-specific annealing of the primer is suppressed, and the specificity of DNA amplification is improved. In addition, as a result of the disappearance of the secondary structure of the template DNA, the elongation ability of DNA polymerase is also improved. The method of the present invention for amplifying a nucleic acid can be carried out under substantially isothermal conditions. In the present invention, the term "isothermal conditions" means that each step is carried out at a substantially constant temperature without significantly changing the reaction temperature in each step.

In the present invention, the time required for incubation of the reaction solution under substantially isothermal conditions is not particularly limited, as long as a target nucleic acid fragment can be amplified. The time for incubation is, for example, from 5 minutes to 12 hours. The incubation time is preferably from 5 minutes to 2 hours, more preferably from 5 minutes to 60 minutes, and further preferably from 5 minutes to 30 minutes. It may also be set from 5 minutes to 15 minutes.

A feature of the method of the present invention for discriminating between the nucleotide sequences of nucleic acids is that it is not necessary to increase or decrease the temperature in a nucleic acid-synthesizing method. In the conventional PCR method, it has been necessary to increase or decrease the temperature, and thus a reactor such as a thermal cycler has been required. However, the method of the present invention can be carried out using only a device for maintaining a constant temperature.

(10) Use of Method of the Present Invention for Discriminating Between Nucleotide Sequences of Nucleic Acids The method of the present invention can be used to discriminate between the nucleotide sequences of nucleic acids. For example, it can be used to detect single nucleotide polymorphisms. Further, it can also be used to discriminate among genotypes, namely, among normal homozygote, mutant homozygote and heterozygote.

An amplification product obtained by the method of the present invention for amplifying a nucleic acid can be detected by methods known to persons skilled in the art. For example, according to gel electrophoresis, a reaction product of a specific size can be detected by staining gel with ethidium bromide. As a detection system for detecting an amplification product, fluorescence polarization, immunoassay, fluorescence energy transfer, enzyme labeling (for example, peroxidase, alkaline phosphatase, etc.), fluorescence labeling (for example, fluorescein, rhodamine, etc.), chemiluminescence, bioluminescence, and the like can be used. It is also possible to detect an amplification product using a labeled nucleotide that is labeled with biotin or the like. In this case, biotin contained in the amplification product can be detected using fluorescently labeled avidin or enzyme-labeled avidin.

The present invention will be more specifically described in the following examples. However, these examples are not intended to limit the scope of the present invention.

EXAMPLES

Example 1

Effect of 3'-Modified Nucleic Acid on Detection of Mutation of β3AR190(T/C)

(1) Preparation of Nucleic Acid Sample Solution Containing Target Nucleic Acid Fragment A β3AR190(T) template hereinafter referred to as Wild type), a β3AR190(C) template (hereinafter referred to as Mutant type), and a β3AR190(T/C) template (hereinafter referred to as Hetero type) (7.5 ng each) were heated with a pretreatment solution (30 mM NaOH and 0.05% Tween20) at 98° C. for 3 minutes, so that each template was converted to a single strand. Thereafter, a sequence in a β3AR gene was amplified under the following conditions.
<Primers>

Primers were designed to target the β3AR gene. The sequence of each primer will be shown below.

```
Primer (1) (Forward):
5'-ATCGTGGCCATCGCCT-3'         (SEQ ID NO: 1)

Primer (2) (Reverse):
5'-CCAGCGAAGTCACGAAC-3'        (SEQ ID NO: 2)
```

This primer set is complementary to β3AR190(M), but it is not complementary to β3AR190(C).
<Mask Oligo>

Figure 4:
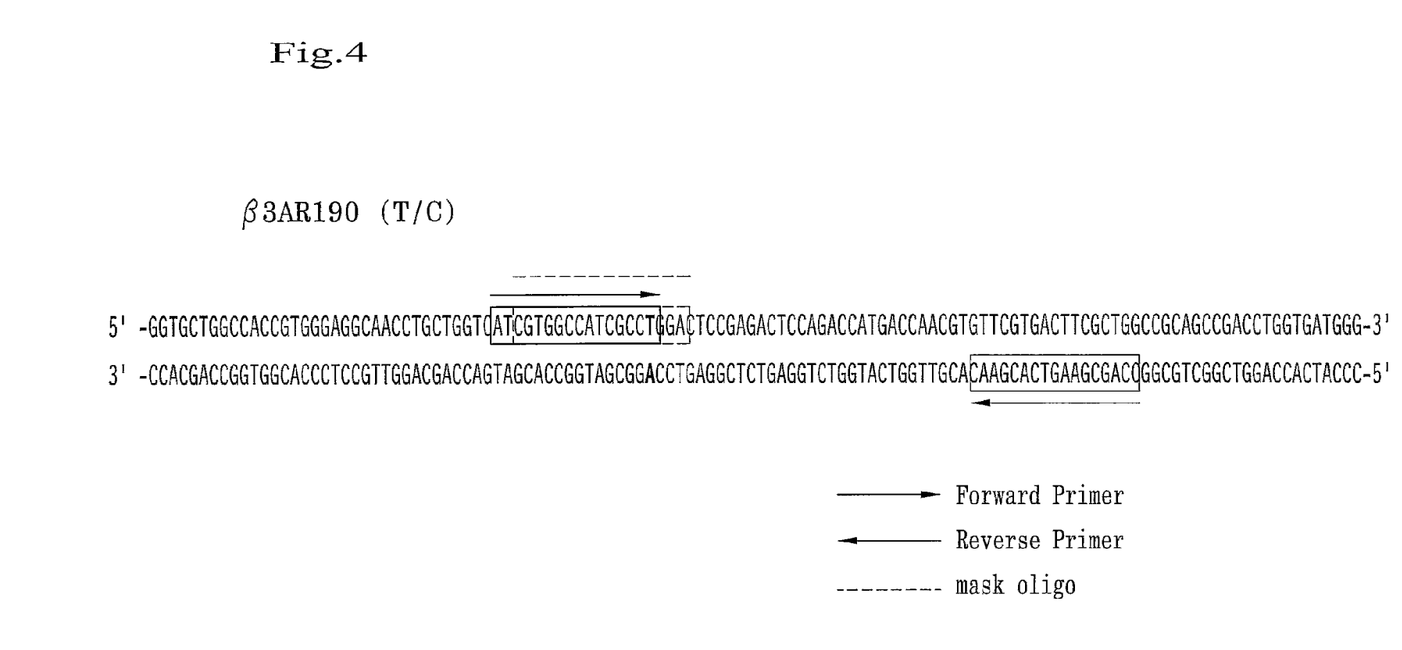
FIG. 4 (SEQ ID NOS: 5 and 6) shows the positional relationship among the forward primer, reverse primer and mask oligo used in the examples.

A modified nucleic acid having a sequence as shown below was added as a mask oligo. The term "Phos" indicates phosphorylation. The positional relationship among the forward primer, reverse primer and mask oligo used in the example is shown in FIG. 4.

```
Mask oligo (3)
5'-CGTGGCCATCGCCCGGA-Phos-3'   (SEQ ID NO: 3)
```

(2) Nucleic Acid Amplification Reaction

An amplification reaction was carried out at 60° C. for 60 minutes in a reaction solution with the following composition. The pH was adjusted to be pH 8.8.
<Composition of Reaction Solution>

| | |
|---|---|
| Tris-HCl | 20 mM |
| KCl | 10 mM |
| (NH$_4$)$_2$SO$_4$ | 10 mM |
| MgSO$_4$ | 8 mM |
| Tween20 | 0.10% |
| DMSO | 5.0% |
| dNTP | each 1.4 mM |
| SYBR Green | Diluted by a factor of 50,000 |
| Primer (1) | 3.6 μM |
| Primer (2) | 3.6 μM |
| Mask oligo (3'-phosphorylated oligo DNA) | 3.6 μM |
| Bst. Polymerase (manufactured by NEB) | 8.0 U |
| Template DNA | 7.5 ng |

(3) Detection of Amplification Product

Figure 1:
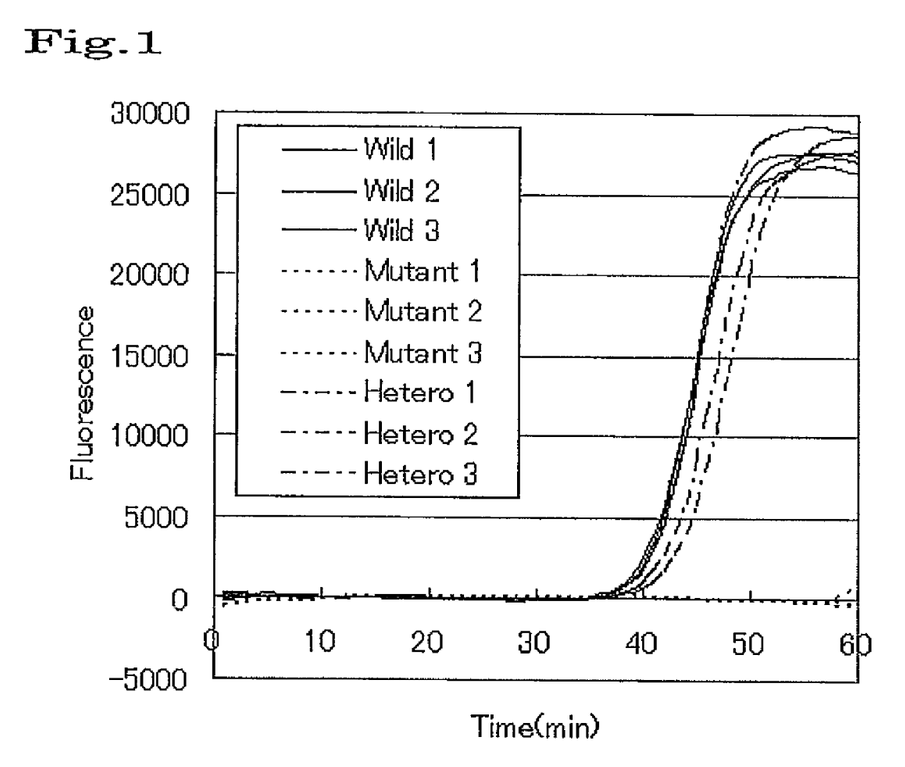
FIG. 1 shows the results of detection of a mutation of β3AR190(T/C) in the case of using 3'-phosphorylated oligo DNA as a mask oligo.

Fluorescence was detected in the amplification reaction product described in (2) above, using a real-time fluorescence detection apparatus (Mx3000p; manufactured by Stratagene). The results are shown in FIG. 1.

It was found that amplification of a nucleic acid took place in a sample from a nucleic acid sample. Using Mx3000p analysis software, the time at which the fluorescence amount reached 250 in the above graph (defined as a Ct value) was calculated. As a result, it was found that Ct=36.2±0.7 minutes in the Wild type (β3AR190(T)), Ct=62.2±3.6 minutes in the Mutant type (β3AR190(C)), and Ct=37.5±0.8 minutes in the Hetero type (β3AR190(T/C)).

Example 2

Effect of RNA on Detection of Mutation of β3AR190(T/C)

(1) Preparation of Nucleic Acid Sample Solution Containing Target Nucleic Acid Fragment A β3AR190(template (hereinafter referred to as Wild type), a β3AR190(C) template (hereinafter referred to as Mutant type), and a β3AR190(T/C) template (hereinafter referred to as Hetero type) (7.5 ng each) were heated with a pre-treatment solution (30 mM NaOH and 0.05% Tween20) at 98° C. for 3 minutes, so that each template was converted to a single strand. Thereafter, a sequence in a β3AR gene was amplified under the following conditions.
<Primers>

Primers were designed to target the β3AR gene. The sequence of each primer will be shown below.

```
Primer (1) (Forward):
5'-ATCGTGGCCATCGCCT-3'         (SEQ ID NO: 1)

Primer (2) (Reverse):
5'-CCAGCGAAGTCACGAAC-3'        (SEQ ID NO: 2)
```

This primer set is complementary to β3AR190(T), but it is not complementary to β3AR190(C).
<Mask Oligo>

RNA having a sequence as shown below was added as a mask oligo. The positional relationship among the forward primer, reverse primer and mask oligo used in the example is shown in FIG. 4.

```
Mask oligo (3)
5'-CGUGGCCAUCGCCCGGA-3'        (SEQ ID NO: 4)
```

(2) Nucleic Acid Amplification Reaction

An amplification reaction was carried out at 60° C. for 60 minutes in a reaction solution with the following composition The pH was adjusted to be pH 8.8.
<Composition of Reaction Solution>

| | |
|---|---|
| Tris-HCl | 20 mM |
| KCl | 10 mM |
| (NH$_4$)$_2$SO$_4$ | 10 mM |
| MgSO$_4$ | 8 mM |

-continued

| | |
|---|---|
| Tween20 | 0.10% |
| DMSO | 5.0% |
| dNTP | each 1.4 mM |
| SYBR Green | Diluted by a factor of 50,000 |
| Primer (1) | 3.6 μM |
| Primer (2) | 3.6 μM |
| Mask oligo RNA | 3.6 μM |
| Bst. Polymerase (manufactured by NEB) | 8.0 U |
| Template DNA | 7.5 ng |

(3) Detection of Amplification Product

Figure 2:
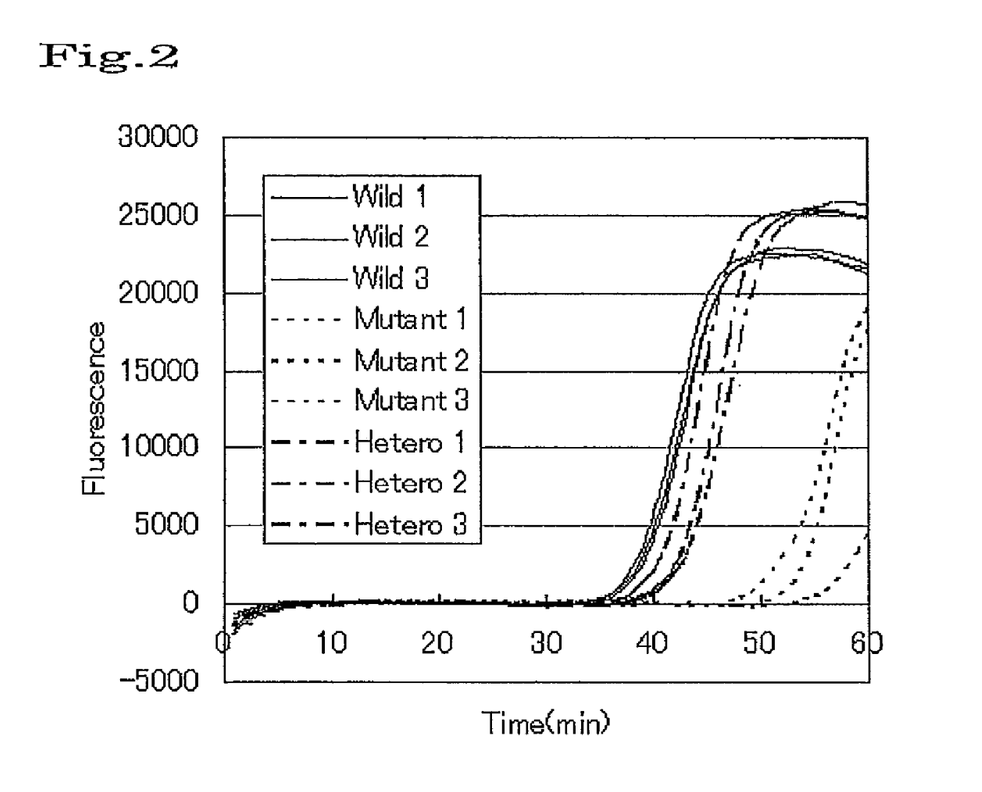
FIG. 2 shows the results of detection of a mutation of β3AR190(T/C) in the case of using RNA as a mask oligo.

Fluorescence was detected in the amplification reaction product described in (2) above, using a real-time fluorescence detection apparatus (Mx3000p; manufactured by Stratagene). The results are shown in FIG. 2.

It was found that amplification of a nucleic acid took place in a sample from a nucleic acid sample. Using Mx3000p analysis software, the time at which the fluorescence amount reached 250 in the above graph (defined as a Ct value) was calculated. As a result, it was found that Ct=34.9±0.4 minutes in the Wild type (β3AR190(T)), Ct=50.8±3.2 minutes in the Mutant type (β3AR190(C)), and Ct=37.8±1.0 minutes in the Hetero type (β3AR190(T/C)).

Comparative Example 1

Detection of Mutation of β3AR190(T/C) in Case of Not Using Mask Oligo (1) Preparation of Nucleic Acid Sample Solution Containing Target Nucleic Acid Fragment A β3AR190(T) template (hereinafter referred to as Wild type), a β3AR190(C) template (hereinafter referred to as Mutant type), and a β3AR190(T/C) template (hereinafter referred to as Hetero type) (7.5 ng each) were heated with a pre-treatment solution (30 mM NaOH and 0.05% Tween20) at 98° C. for 3 minutes, so that each template was converted to a single strand. Thereafter, a sequence in a β3AR gene was amplified under the following conditions.

<Primers>

Primers were designed to target the β3AR gene. The sequence of each primer will be shown below.

```
Primer (1) (Forward):
5'-ATCGTGGCCATCGCCT-3'        (SEQ ID NO: 1)

Primer (2) (Reverse):
5'-CCAGCGAAGTCACGAAC-3'       (SEQ ID NO: 2)
```

This primer set is complementary to β3AR190(I), but it is not complementary to β3AR190(C).

(2) Nucleic Acid Amplification Reaction

An amplification reaction was carried out at 60° C. for 60 minutes in a reaction solution with the following composition. The pH was adjusted to be pH 8.8.

<Composition of Reaction Solution>

| | |
|---|---|
| Tris-HCl | 20 mM |
| KCl | 10 mM |
| (NH$_4$)$_2$SO$_4$ | 10 mM |
| MgSO$_4$ | 8 mM |
| Tween20 | 0.10% |
| DMSO | 5.0% |
| dNTP | each 1.4 mM |
| SYBR Green | Diluted by a factor of 50,000 |
| Primer (1) | 3.6 μM |
| Primer (2) | 3.6 μM |
| Bst. Polymerase (manufactured by NEB) | 8.0 U |
| Template DNA | 7.5 ng |

(3) Detection of Amplification Product

Figure 3:
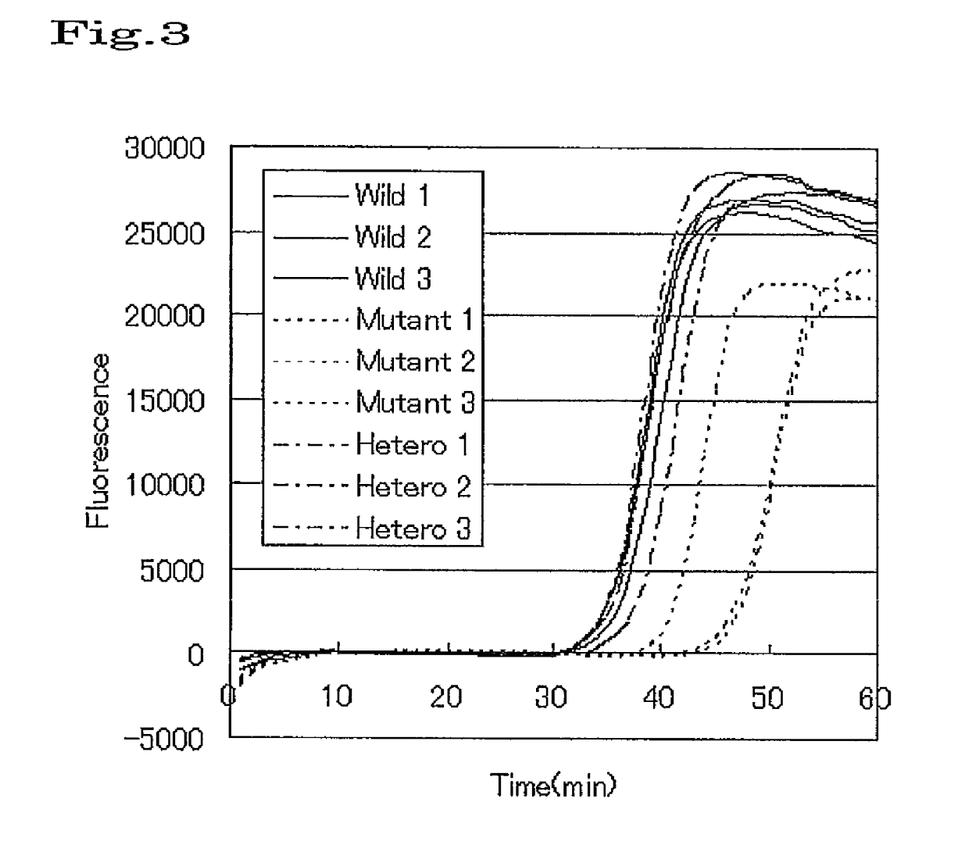
FIG. 3 shows the results of detection of a mutation of β3AR190(T/C) in the case of not using such a mask oligo.

Fluorescence was detected in the amplification reaction product described in (2) above, using a real-time fluorescence detection apparatus (Mx3000p; manufactured by Stratagene). The results are shown in FIG. 3.

It was found that amplification of a nucleic acid took place in a sample from a nucleic acid sample. Using Mx3000p analysis software, the time at which the fluorescence amount reached 250 in the above graph (defined as a Ct value) was calculated. As a result, it was found that Ct=31.5±0.3 minutes in the Wild type (β3AR190(T)), Ct 41.6±3.0 minutes in the Mutant type (β3AR190(C)), and Ct=32.4±12 minutes in the Hetero type (β3AR190(T/C)).

The invention claimed is:

1. A method for discriminating between the nucleotide sequence of a first nucleic acid and the nucleotide sequence of a second nucleic acid in a nucleic acid sample, the method comprising the steps of:
   (i) providing a reaction solution, comprising
       at least one type of deoxynucleotide triphosphate,
       a DNA polymerase having a strand displacement ability,
       the nucleic acid sample as a template,
       an oligonucleotide primer (1) and an oligonucleotide primer (2), and
       an oligonucleic acid (hereinafter "mask oligo");
   (ii) incubating the reaction solution under isothermal conditions to carry out a polymerase reaction and to produce an amplification product thereof;
   (iii) detecting the amplification product and measuring an amplification rate of the amplification product; and
   (iv) using the measured amplification rate as an indicator to discriminate between the nucleotide sequence of the first nucleic acid and the nucleotide sequence of the second nucleic acid in the nucleic acid sample, wherein the oligonucleotide primer (1) is more complementary to the first nucleic acid than to the second nucleic acid, and the oligonucleotide primer (2) hybridizes to a portion of an elongation product of the oligonucleotide primer (1), wherein said portion is located 3' downstream of the nucleotide sequence of the oligonucleotide primer (1) in said elongation product, wherein the mask oligo hybridizes to the nucleotide sequence portions of the first nucleic acid and the second nucleic acid to be discriminated, wherein the mask oligo is more complementary to the second nucleic acid than to the first nucleic acid, wherein the mask oligo does not become an origin of an elongation reaction with the polymerase for any nucleic acid template, and wherein a portion of the oligonucleotide primer (1) and a portion of the mask oligo hybridize to the same nucleotide sequence portions of the first nucleic acid and the second nucleic acid.

2. The method according to claim 1, wherein the nucleotide sequence portions of the first nucleic acid and the second nucleic acid, to which both the oligonucleotide primer (1) and the mask oligo hybridize, hybridize to a region comprising the 3'-terminus of the oligonucleotide primer (1).

3. The method according to claim 1, wherein the nucleotide sequence portions of the first nucleic acid and the second nucleic acid, to which both the oligonucleotide primer (1) and the mask oligo hybridize, hybridize to a region comprising the 5'-terminus of the mask oligo.

4. The method according to claim 1, wherein the oligonucleotide primer (1) is designed to hybridize to the first nucleic acid or the second nucleic acid via only a consecutive region at the 3'-terminus.

5. The method according to claim 1, wherein there is a single nucleotide polymorphism relationship between the first nucleic acid and the second nucleic acid.

6. The method according to claim 1, wherein the reaction solution further comprises at least 0.01% of a surfactant.

7. The method according to claim 6, wherein the reaction solution further comprises at least 0.05% of a surfactant.

8. The method according to claim 6, wherein the surfactant is a nonionic surfactant.

9. The method according to claim 8, wherein the HLB value of the nonionic surfactant is 12 or greater.

10. The method according to claim 9, wherein the HLB value of the nonionic surfactant is 14 or greater.

11. The method according to claim 8, wherein the nonionic surfactant is selected from the group consisting of: polyoxyethylene sorbitan fatty acid ester nonionic surfactants and polyoxyethylene alkyl ether nonionic surfactants.

12. The method according to claim 11, wherein the polyoxyethylene sorbitan fatty acid ester nonionic surfactant is a polyoxyethylene sorbitan monofatty acid ester.

13. The method according to claim 12, wherein the polyoxyethylene sorbitan monofatty acid ester is represented by the following chemical formula:

wherein x+y+z+w=20; and R represents an alkyl group containing 12 to 18 carbon atoms.

14. The method according to claim 13, wherein the polyoxyethylene sorbitan fatty acid ester nonionic surfactant is at least one selected from the group consisting of: polyoxyethylene (20) sorbitan monolaurate, polyoxyethylene (20) sorbitan monopalmitate, polyoxyethylene (20) sorbitan monostearate, and polyoxyethylene (20) sorbitan monooleate.

15. The method according to claim 1, wherein the reaction solution further comprises a divalent cation.

16. The method according to claim 1, wherein the reaction solution further comprises a melting temperature adjuster.

17. The method according to claim 1, wherein the DNA polymerase having a strand displacement ability is selected from the group consisting of 5'→3' exonuclease-deficient Bst DNA polymerase derived from *Bacillus stearothermophilus*, 5'→3' exonuclease-deficient Bca DNA polymerase derived from *Bacillus caldotenax*, and 5'→3' exonuclease-deficient Vent DNA polymerase derived from *Thermococcus litoralis*.

18. The method according to claim 1, wherein the reaction solution is incubated under isothermal conditions from 50° C. to 100° C.

19. The method according to claim 1, wherein the time required for the incubation of the reaction solution under isothermal conditions is 60 minutes or shorter.

* * * * *